US00PP30127P3

(12) United States Plant Patent
Brand

(10) Patent No.: US PP30,127 P3
(45) Date of Patent: Jan. 22, 2019

(54) BARBERRY PLANT NAMED 'UCONNBTB048'

(50) Latin Name: *Berberis thunbergii*
Varietal Denomination: UCONNBTB048

(71) Applicant: University of Connecticut, Farmington, CT (US)

(72) Inventor: Mark Brand, Farmington, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 15/330,050

(22) Filed: Jul. 30, 2016

(65) Prior Publication Data

US 2018/0035588 P1 Feb. 1, 2018

(51) Int. Cl.
*A01H 5/00* (2018.01)
*A01H 5/08* (2018.01)

(52) U.S. Cl.
USPC ..... Plt./241
CPC ..... *A01H 5/08* (2013.01)

(58) Field of Classification Search
USPC ..... Plt./241
See application file for complete search history.

(56) References Cited

U.S. PATENT DOCUMENTS

PP8,215 P 4/1993 Moretti

OTHER PUBLICATIONS

Lehrer et al (Scientia Horticulturae. 2008. 119:67-71).*
Co-pending U.S. Appl. No. 15/330,051, filed Jul. 30, 2016.
Co-pending U.S. Appl. No. 15/330,049, filed Jul. 30, 2016.
Co-pending U.S. Appl. No. 15/330,048, filed Jul. 30, 2016.

* cited by examiner

*Primary Examiner* — Keith O. Robinson
(74) *Attorney, Agent, or Firm* — Michael Best & Friedrich LLP

(57) ABSTRACT

The present invention relates to a new and distinct cultivar of Barberry plant, botanically known as *Berberis thunbergii* and hereinafter referred to by the name 'UCONNBTB048'. The unique characteristics of this new Barberry plant include seed sterile; compact, dense, low-growing habit; thick and slightly leathery bright yellow spring foliage and light yellow and chartreus summer foliage; adaptable to many landscape situations; resistant to black stem rust disease; and winter cold hardy to at least −26° C.

5 Drawing Sheets

FEDERAL FUNDING

This invention was made with government support under 2015-31200-06009 awarded by the USDA. The government has certain rights in the invention.

BACKGROUND OF THE INVENTION

The present invention relates to a new and distinct cultivar of Barberry plant, botanically known as *Berberis thunbergii* and hereinafter referred to by the name 'UCONNBTB048'.

The new Barberry plant is a product of a planned breeding program conducted in Storrs, Conn. The new Barberry plant was developed by exposing pre-germinated seed to the mitotic inhibitor colchicine to create an autotetraploid plant. Specific methods used followed those published in Lehrer, J. M., M. H. Brand, J. D. Lubell, "Induction of tetraploidy in meristematicaly active seeds of Japanese barberry (*Berberis thunbergii* var. *atropurpurea*) through exposure to colchicine and oryzalin", *Scientia Horticulturae* 119:67-71 (2008). Briefly, seeds were cold stratified for 4-6 weeks and then pre-germinated seeds with 5 -7 mm of radicle emergence were exposed to a 0.1% colchicine solution for 24 hours. The maternal parent plant that provided the seed is *Berberis thunbergii* 'Bogozam' Bonanza Gold. 'Bogozam' is a patented variety receiving Plant Pat. No. 8,215 on Apr. 27, 1993. The paternal parent is unknown since the seed used was open pollinated. Treated seeds planted in flats and grown in a greenhouse until they were large enough for ploidy analysis by flow cytometry. Seedlings that were tetraploids were grown on for further evaluation. Tetraploidy was confirmed multiple times by flow cytometry when plants were in containers and the field.

In early 2007, fourteen tetraploid plants were created and grown in a greenhouse and a coldframe for their first growing season. Tetraploid plants were grown outdoors in containers during 2008, 2009 and 2010 and were evaluated for horticultural traits and fruit and seed production. In spring 2011, tetraploid plants were planted in the field for long term evaluation. Diploid *Berberis thunbergii* 'Bogozam' Bonanza Gold plants were grown in the same planting as the tetraploid plants to serve as control plants. During the growing seasons of 2012, 2013, and 2014, tetraploid plants established in the field were evaluated for fruit production, seed production, seed germination and seedling ploidy in comparison to diploid control plants. *Berberis thunbergii* 'UCONNBTB048' was selected from among the 14 tetraploid seedlings based on lack of seed production, compact, dense form, and attractive yellow foliage color.

Asexual reproduction of *Berberis thunbergii* 'UCONNBTB048' by softwood stem cuttings (since 2012) made in late June through early July in a greenhouse or container nursery environment has shown that the unique features of this new barberry plant are stable and reproduced true-to-type in successive generations of asexual reproduction.

SUMMARY OF THE INVENTION

Plants of the new Barberry have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of the new Barberry plant: dense habit growing to approximately 60 cm tall by 90 cm wide in 10 years; bright yellow spring foliage and light yellow and chartreus summer foliage; foliage develops a narrow orange edge as it matures from early spring to summer; foliage thick and slightly leathery, held on stout stems; fall foliage color is orange; small yellow flowers held in clusters of 3 to 6 flowers, in late April-early May in Connecticut, not as plentiful as is typical for yellow foliage cultivars; rare fruit is red in October, ellipsoidal, 7-10 mm long and 4-5 mm wide; cold hardy in winter to at least −26° C.; has not produced any seeds to date, while the diploid maternal parent *Berberis thunbergii* 'Bogozam' Bonanza Gold produces many viable seeds; tested to be resistant to black stem rust by the USDA Cereal Diseases Laboratory in St. Paul, Minn.

These characteristics in combination distinguish *Berberis thunbergii* 'UCONNBTB048' as a new and distinct Barberry plant:

1. seed sterile;
2. compact, dense, low-growing habit;
3. thick and slightly leathery bright yellow spring foliage and light yellow and chartreus summer foliage;
4. adaptable to many landscape situations;
5. resistant to black stem rust disease; and
6. winter cold hardy to at least −26° C.

Plants of the new Barberry can be compared to plants of the female parent *Berberis thunbergii* 'Bogozam' Bonanza Gold. Plants of the new Barberry differ primarily from plants of 'Bogozam' in that 'UCONNBTB048' is sterile, while the diploid maternal parent 'Bogozam' can produce over 1,500 seeds per plant per year. In addition, 'UCONNBTB048' grows slightly taller than 'Bogozam', but has a similar width and comparable density and fullness. The leaves of 'UCONNBTB048' are approximately two times larger than 'Bogozam', thicker and more leathery, with color being about the same. 'UCONNBTB048' stems are stouter and larger in diameter than 'Bogozam'.

Plants of the new Barberry can be compared to the unpatented commercial variety *Berberis* 'Emerald Carousel'. These varieties are similar in most horticultural characteristics; however 'UCONNBTB048' differs in the following:

1. Very compact plant habit, whereas this comparator is a large plant with a spreading habit.
2. Yellow leaf color, whereas this comparator has a green leaf color.
3. Very low or no female fertility or fruit production, whereas this comparator is highly fruitful.

BRIEF DESCRIPTION OF THE PHOTOGRAPHS

The accompanying colored photographs illustrate the overall appearance of the new Barberry plant showing the colors as true as it is reasonably possible to obtain in colored reproductions of this type. Colors in the photographs may differ slightly from the color values cited in the detailed botanical description which accurately describe the colors of the new Barberry plant.

DETAILED BOTANICAL DESCRIPTION

Figure 1:
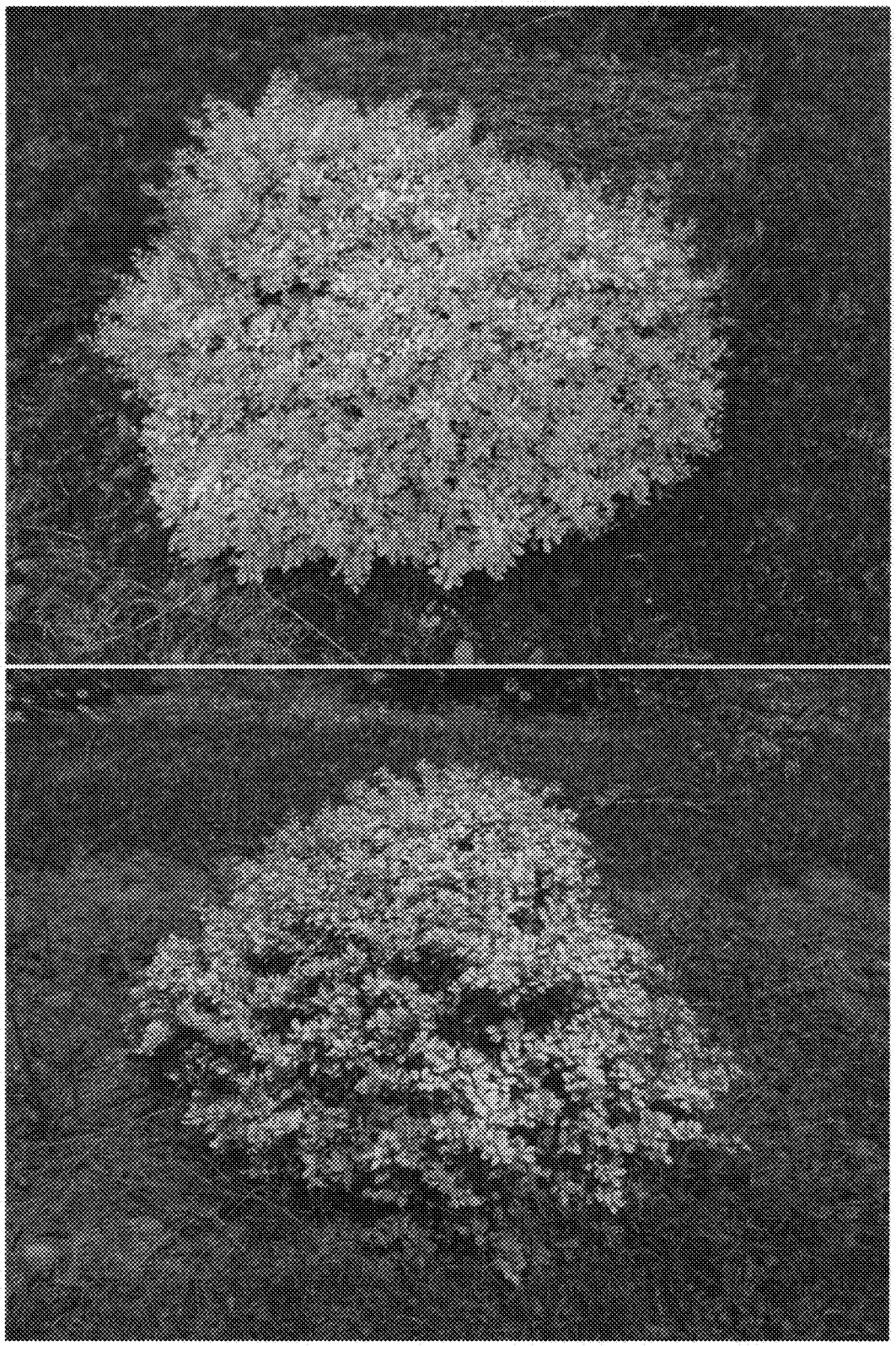
FIG. 1 is a photograph showing a field grown plant of 'UCONNBTB048' as it appears in spring (top image) and then later in the summer (bottom image).
Figure 2:
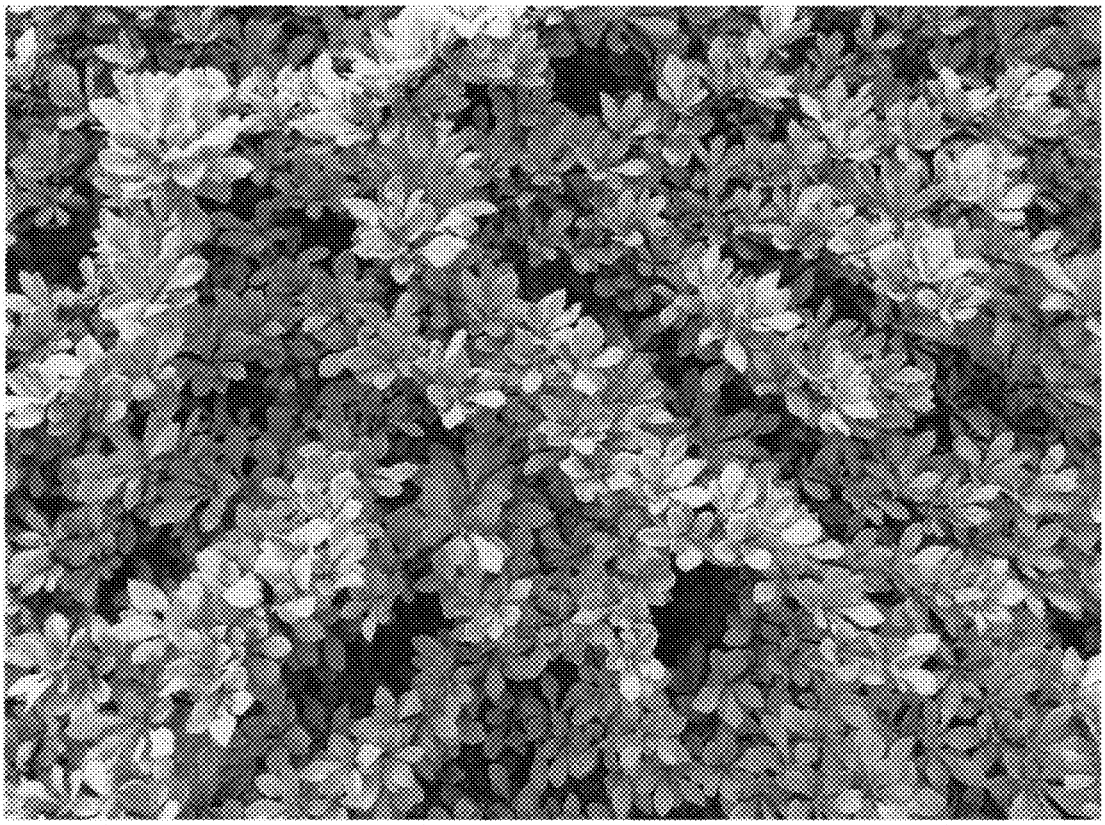
FIG. 2 is a photograph showing a close up of 'UCONNBTB048' foliage in the spring prior to long shoot extension.
Figure 3:
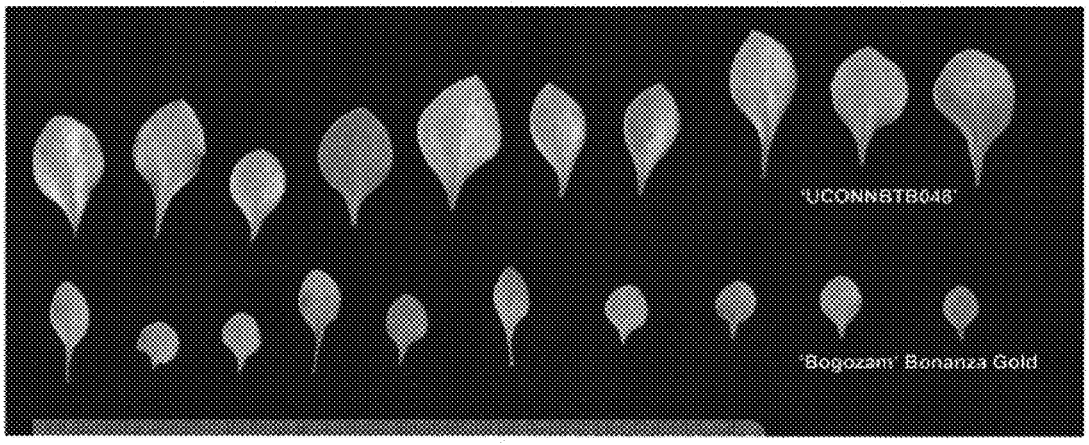
FIG. 3 is photographs showing a close up comparison of leaves from 'Bogozam' (bottom row) and 'UCONNBTB048' (top row).
Figure 4:
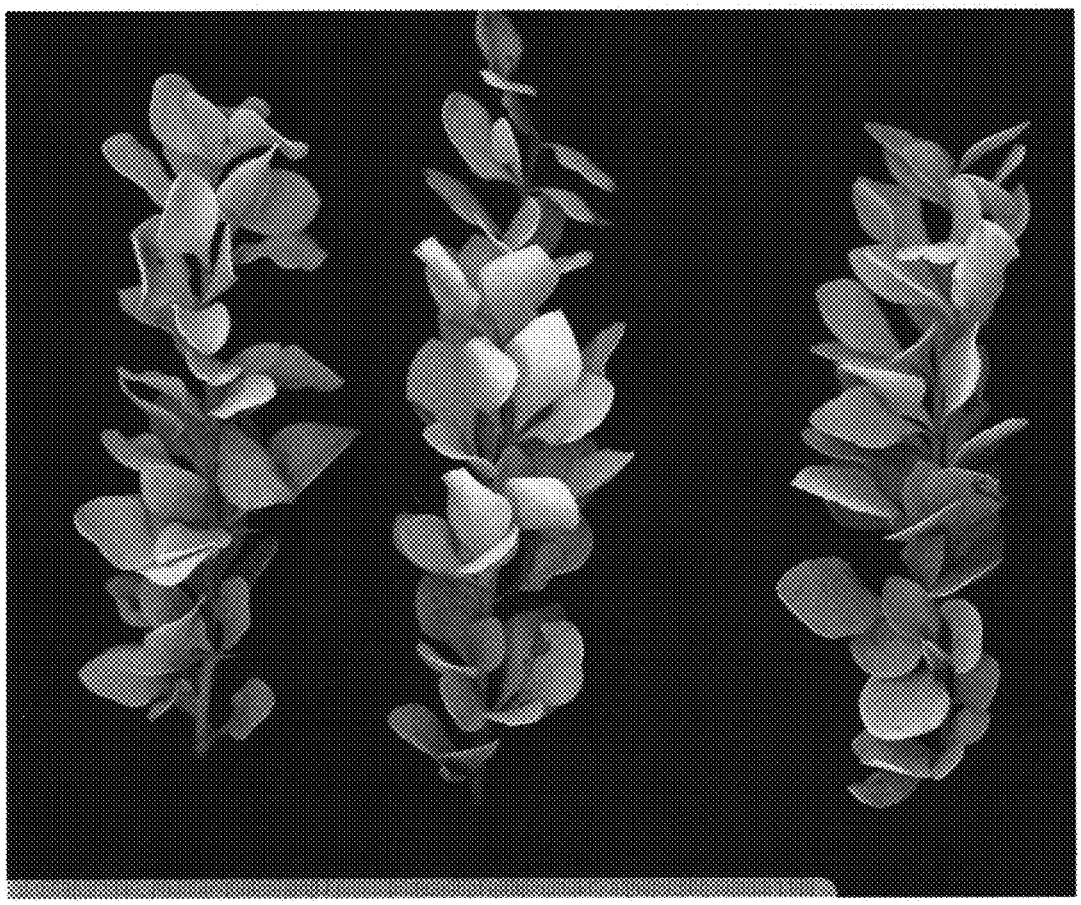
FIG. 4 is photographs showing the summer shoots of 'UCONNBTB048'.
Figure 5:
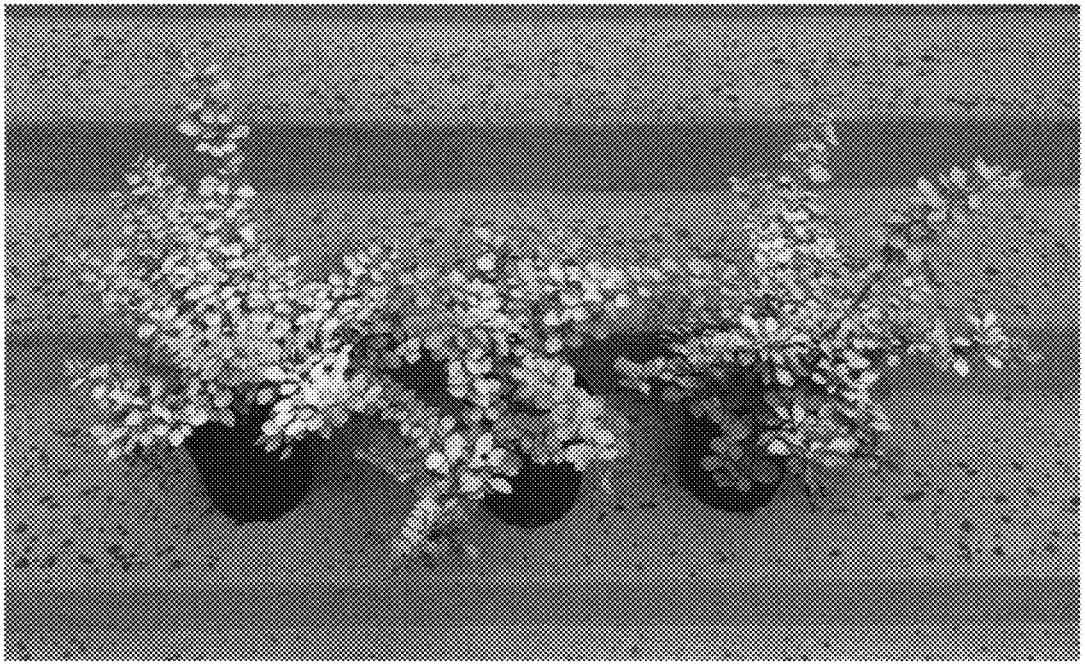
FIG. 5 is photographs showing three container grown plants of 'UCONNBTB048' at the beginning of their second summer of growth since propagation. These plants were rooted from softwood cuttings two summers prior.

The aforementioned photographs and following observations, measurements and values describe plants grown during the spring, summer, or fall in ground beds or container, in an outdoor nursery in Storrs, Conn. and under cultural practices which closely approximate commercial Barberry production. Plants used for most photographs and description were 10 years old. In the following detailed description, color references are made to The Royal Horticultural Society Colour Chart, 1995 Edition, except where general terms of ordinary dictionary significance are used.

Botanical classification: *Berberis thunbergii* 'UCONNBTB048'.

Parentage:

*Female, or seed, parent.*—*Berberis thunbergii* 'Bogozam' Bonanza Gold.

*Male, or pollen, parent.*—Unknown. Open pollinated seed was used to create the new barberry.

Propagation:

*Type.*—Softwood stem cutting.

*Time to initiate roots, summer.*—About 6 weeks at daytime temperatures between 75-90° F.

*Time to produce a rooted young plant, summer.*—About 8-12 weeks at temperatures between 75-90° F.

*Root description.*—2-6 roots per cutting, yellow to brown in color and not effectively measured with a color chart.

*Rooting habit.*—Fibrous root system develops from the initial adventitious roots.

Plant description:

*Plant form and growth habit.*—Low, dense, mounded, compact plant, typically wider than tall.

*Plant height.*—About 60 cm tall in 10 years.

*Plant diameter* (*area of spread*).—About 90 cm wide in 10 years.

*Plant vigor.*—Medium.

Lateral branch description:

*Length.*—About 15 cm, typically between 10-20 cm.

*Diameter.*—About 2 mm to 3 mm.

*Internode length.*—About 12 mm, typically between 10-20 mm.

*Aspect.*—Upright and arching outward from the plant center.

*Strength.*—Firm and stiff.
*Texture.*—Fine.
*Color.*—Close to 146D yellow-green on new, current season shoots, then changing to close to 200B brown group as the stems mature. Stems older than 1-2 seasons have a color closer to 199D.
*Thorns.*—Quantity: single at most nodes. Length: 9-10 mm. Width at the base: 1 mm. Color: 146D yellow-green.

Leaf description:
*Arrangement.*—Whorled in rosette on spur shoots; alternate down long shoots, but typically 2-4 leaves at each node.
*Length.*—About 35 mm, typically ranging from 20-40 mm.
*Width.*—About 20 mm, typically ranging from 15-23 mm.
*Shape.*—Obovate to spatulate-oblong.
*Apex.*—Typically obtuse, sometimes with small spine at tip.
*Base.*—Narrowing to only petiole; very acute.
*Margin.*—Entire.
*Texture, upper and lower surfaces.*—Glabrous.
*Venation pattern.*—Pinnate.
*Color.*—Developing leaves, upper surface: Close to yellow group 6A to 6C, 7A to 7C and 10A on the upper surface under high light conditions. The new growth has a red coloration visible for a period at the leaf margin and on the new leaf shoots that approximates red group 43A.
*Developing leaves, lower surface.*—Close to yellow group 10B to 10D under high light conditions.
*Fully expanded leaves, upper surface.*—Leaves on the interior of the plant will range from 141A green group through 144A yellow-green group to 11A to 11D when fully exposed to sun under high light conditions.
*Fully expanded leaves, lower surface.*—Close to 11B to 11D yellow group under high light conditions. Shaded leaves 138B green group.
*Petiole.*—Length: About 1-12 mm. Diameter: About 1mm. Texture, upper and lower surfaces: glabrous. Color, upper and lower surfaces: RHS 12C yellow.
*Persistence of foliage.*—Deciduous.
*Glossiness of the leaf.*—Medium.

Flower description:
*Flower arrangement and habit.*—Typically cymous.
*Fragrance.*—None noted.
*Natural flowering season.*—April in Storrs, Conn.
*Flower longevity.*—7 to 14 days depending on weather conditions.
*Inflorescence length.*—About 15 mm; ranging from about 10-20 mm.
*Inflorescence diameter.*—About 22.5 mm; ranging from about 21-25 mm.
*Inflorescence type.*—Umbellate fascicles. Axial occurring along underside of branches.
*Number of flowers per inflorescence.*—3-6.
*Flower diameter.*—About 12 mm; ranging from 10-13 mm.
*Flower length (height).*—About 5.75 mm; ranging from 5-7 mm.
*Flower buds.*—Length: About 4 mm. Diameter: About 6 mm. Shape: Rounded. Color: Close to 11A and 11B yellow group, with highlights of 43A and 43B red group.
*Petals.*—Arrangement: 6 petals in a single whorl.
*Length.*—About 4-5 mm.
*Width.*—About 3-4 mm.
*Shape.*—Cupped.
*Apex.*—Rounded to acute.
*Margin.*—Smooth.
*Texture, upper and lower surfaces.*—Both glabrous.
*Color.*—When opening and fully open, adaxial and abaxial surfaces: 12C yellow group.
*Sepals.*—Arrangement: 6 to 8 sepals in a single whorl. Length: About 7 mm. Width: About 4 mm. Shape: cupped. Apex: rounded to acute. Base: straight-sided, tapering. Margin: smooth. Texture, upper and lower surfaces: glabrous. Color: Fully developed, adaxial surface: Close to 12C, yellow group, with colors from abaxial side showing through. Fully developed, abaxial surface: Close to 12C yellow group base color, with highlights of 43A and 43B, red group.
*Peduncles.*—Length: About 4-14 mm. Diameter: About 1 mm. Aspect: About 60 degrees from lateral branch axis. Color: Close to 154B yellow-green group.
*Pedicels.*—Length: About 4-6 mm. Diameter: About 1 mm. Aspect: About 45-60 degree from peduncle axis. Color: Close to 154B yellow-green group.
*Reproductive organs.*—Stamens: Quantity: 6. Anther shape: flat to cupped, narrow. Anther length: About 4 mm. Anther color: Close to 12C. Pollen amount: Scarce and sticky. Pollen color: Near RHS yellow 12A. Pistils: Quantity: 1 per flower. Pistil length: About 3 mm. Style length: About 1-2 mm. Style color: Close to 154B yellow-green. Stigma color: Close to 154B yellow-green. Ovary color: Close to 154B yellow-green. Seeds and fruits: Fruit development has been observed on plants of the new Barberry, but only a very small number of fruits have been observed. To date, fruits have been devoid of seeds. Fruit shape: Elliptical, 7-10 mm long and 4-5 mm in diameter. Fruit color: RHS color near red 53B. Fruit waxiness: Glossy.

Garden performance: Plants of the new Barberry have been observed to have excellent garden performance and tolerate a wide range of environmental conditions and temperatures ranging from about −26° C. to about 40° C.

Pathogen & pest resistance: Plants of the new Barberry have been observed to be resistant to blackstem rust (*Puccinia graminis* f. sp. *tritici*). Plants of the new Barberry have not been shown to be resistant to pests and other pathogens common to Barberry plants.

It is claimed:

1. A new and distinct Barberry plant named 'UCONNBTB048' as illustrated and described.

* * * * *